United States Patent [19]

Vanover et al.

[11] Patent Number: 5,002,678

[45] Date of Patent: Mar. 26, 1991

[54] LUBRICANTS FOR HEAT TRANSFER FLUIDS

[75] Inventors: Arthur R. Vanover, Brandenburg; Jerry D. Necessary, Elizabethtown, both of Ky.; Kiran B. Chandalia, Cheshire, Conn.; John W. Reisch, Guilford, Conn.; James M. O'Connor, Branford, Conn.; Kevin Delaney, Cromwell, Conn.; Philip R. Miller, Hamden, Conn.

[73] Assignee: Olin Corporation, Cheshire, Conn.

[21] Appl. No.: 546,468

[22] Filed: Jun. 29, 1990

[51] Int. Cl.⁵ .................... C09K 5/04; C07C 43/12
[52] U.S. Cl. .................... 252/68; 252/52 A; 252/54; 252/67; 568/614; 568/615
[58] Field of Search ............ 568/614, 615; 252/52 A, 252/68, 67

[56] References Cited

U.S. PATENT DOCUMENTS

| | | | |
|---|---|---|---|
| 2,837,574 | 6/1958 | Hill et al. | 568/614 |
| 3,190,926 | 6/1965 | Edwards | 252/52 A |
| 3,623,988 | 11/1971 | Weimer | 568/614 |
| 3,666,671 | 5/1972 | Kalopissis et al. | 568/614 |
| 3,829,508 | 8/1974 | Diery et al. | 568/614 |
| 3,941,849 | 3/1976 | Herold | 260/607 |
| 4,335,188 | 6/1982 | Igi et al. | 428/458 |
| 4,472,560 | 9/1984 | Kuyper et al. | 526/120 |
| 4,477,589 | 10/1984 | van der Hulst et al. | 502/169 |
| 4,605,784 | 8/1986 | Eubanks et al. | 568/614 |
| 4,755,316 | 7/1988 | Magid et al. | 252/68 |
| 4,948,525 | 8/1990 | Sasaki et al. | 252/68 |

FOREIGN PATENT DOCUMENTS

| | | | |
|---|---|---|---|
| 200403 | 11/1986 | European Pat. Off. | 568/614 |
| 0331171 | 3/1989 | European Pat. Off. | |
| 021632 | 2/1984 | Japan | 252/68 |
| 161938 | 8/1985 | Japan | 568/614 |
| 916096 | 1/1963 | United Kingdom | 568/614 |
| 2216541 | 10/1989 | United Kingdom | |

Primary Examiner—Jacqueline V. Howard
Assistant Examiner—Ellen M. McAlvoy
Attorney, Agent, or Firm—Dale Lynn Carlson

[57] ABSTRACT

A heat transfer composition comprising a heat transfer medium and a lubricant, wherein said heat transfer medium is a low boiling organic compound and wherein said lubricant is a halogenated polyoxyalkylene monoalcohol having the empirical structural formula:

$$R_1X_m(OR_2)_n-OH$$

wherein $R_1$ and $R_2$ are independently selected from the group having 1 to 18 carbon atoms, an aryl group having from 6 to 18 carbon atoms, and combinations thereof, X is a halogen, m is an integer of between 1 and 37, and n is an integer from 5–350. Also claimed is the process for making the lubricant and the lubricant composition itself.

13 Claims, No Drawings

LUBRICANTS FOR HEAT TRANSFER FLUIDS

BACKGROUND OF THE INVENTION

The use of lubricants in heat transfer devices of the mechanical vapor recompression type, including refrigerators, heat pumps and air conditioning systems, is well known. In such devices, a working fluid of suitable boiling point evaporates at low pressure taking heat from the surrounding zone. The resulting vapor is then compressed and passed to a condenser where it condenses and gives off heat to a second zone. The condensate is then returned through an expansion valve to the evaporator, so completing the cycle. The mechanical energy required for compressing the vapor and pumping the fluid is provided by, for example, an electric motor or an internal combustion engine. As is the case with other mechanical equipment, it is necessary for the moving parts of the heat transfer devices to be adequately lubricated and the devices are generally designed to use lubricants which are miscible with the working fluids.

In the past, the heat transfer fluids typically used in these heat transfer devices were chlorofluorocarbons, such as dichlorodifluoromethane, together with a lubricant such as mineral oil. Today, the production of several of these chlorofluorocarbons is being severely limited by international agreement in order to protect the stratospheric ozone layer.

Unfortunately, some of the compounds, such as, for example, 1,1,1,2-tetrafluoroethane, which are being proposed as working fluids to replace dichlorodifluoromethane, are insufficiently miscible with mineral oils to allow the latter to be used as lubricants with these working fluids. Polyalkylene glycols have been proposed as alternative lubricants, but they are not entirely satisfactory for a number of reasons. For example, while polyalkylene glycols exhibit desired reverse solubility above a certain temperature such that the working fluid tends to separate from the lubricant, for example at temperatures above about 40° C., they often attract water in an amount sufficient to cause corrosion in the equipment. More specifically, monols which rely upon ethylene oxide content to achieve sufficient miscibility and viscosity to permit their use as lubricants, such as is disclosed in European Patent application 336,171 assigned to Nippon Oil Co., Ltd., and polypropylene glycol diols and triols such as is disclosed in U.S. Pat. No. 4,755,316 assigned to Allied-Signal Inc. all tend to attract more water than might be desired. Furthermore, these compounds often fail to wet metals sufficiently to provide efficient lubrication and have an adverse effect on aluminium commonly used for the construction of compressors.

The discovery of new lubricants for hydrofluorcarbon working fluids that do not suffer from the water affinity problems and the lack of wetting efficacy associated with known polyalkylene glycols, when utilized in a fluorocarbon working fluid, would be highly desired by the heat transfer fluids community. Heretofore, an entirely satisfactory solution to those problems has not been proposed to the knowledge of the present inventors.

SUMMARY OF THE INVENTION

In one aspect, the present invention relates to a halogenated polyoxyalkylene monoalcohol compound having the empirical structural formula:

$$R_1X_m(OR_2)_n-OH$$

wherein $R_1$ is selected from the group consisting of a straight or branched-chain alkyl group having 1 to 18 carbon atoms, an aryl group having from 6 to 18 carbon atoms, and combinations thereof, X is a halogen, m is an integer of between 1 and 37, and n is an integer from 5–350, preferably from about 10–50.

In another aspect, the present invention relates to a heat transfer composition comprising a heat transfer medium and a lubricant, wherein said heat transfer medium is a low boiling organic compound and wherein said lubricant is a halogenated polyoxyalkylene monoalcohol having the above identified empirical structural formula. The lubricant preferably has a molecular weight of at least about 500 and a viscosity of between about 20 cst. and about 320 cst.

In yet another aspect, the present invention relates to a process for producing a halogenated polyoxyalkylene monoalcohol having a molecular weight of between about 500 and about 20,000 by a reaction comprising:

(a) alkoxylating a halogenated monoalcohol in the presence of an acid or base catalyst to produce an alkoxylated halogenated monoalcohol having a molecular weight of between about 200 and about 500, and (b) reacting said alkoxylated halogenated monoalcohol with an alkylene oxide in the presence of a double metal cyanide catalyst to produce a halogenated polyoxyalkylene monoalcohol having a molecular weight of between about 500 and about 20,000.

DETAILED DESCRIPTION OF THE INVENTION

In accordance with the present invention, it has now been surprisingly found that a halogenated polyoxyalkylene monoalcohol having a molecular weight of at least about 500 (preferably at least about 600) is produced utilizing the two-step process of the present invention. This result is particularly unexpected since prior attempts to make these monoalcohols using conventional acid or base propoxylation catalysts provided a loss of catalyst activity after the addition of 7–10 moles of propylene oxide. Subsequent catalyst additions did not provide the desired higher molecular weight monoalcohol product. In contrast, the use of the double metal cyanide complex ("DMC") catalyst to increase the molecular weight of the monoalcohol after the inital propoxylation of trifluoroethanol with an acid or base catalyst provides a product having advantageous molecular weight and viscosity properties. The resulting halogenated polyoxyalkylene monoalcohol provides excellent utility as a lubricant for heat transfer media, particularly chlorofluorocarbon or hydrochlorofluorocarbon heat transfer media.

It has also been surprisingly found in accordance with the process of the present invention that the use of acid catalyst(s) in the production of propoxylated precursors for polyols makes it possible to produce the desired high molecular weight halogenated polyoxyalkylene monoalcohols directly in a DMC-catalyzed reaction without purification of the propoxylated precursors. Thus, the acid catalysts provide the desired catalysis for producing propoxylated precursors without deactivating or otherwise adversely affecting the DMC catalyst. Therefore, steps (a) and (b) of the process of the present invention can be conducted simultaneously or sequentially without catalyst residue removal prior to carrying out step (b) of the process. This result will be of significant value to lubricant manufacturers since it avoids the need to purify the propoxylated precursors prior to contacting with the DMC catalyst which is typically required if a base catalyst is utilized in step (a) of the process of the present invention.

The acid catalyst(s) useful in the process of the present invention are preferably Lewis acids, such as $BF_3Et_2O$ (boron trifluoride etherate), $SbF_5$ (antimony pentafluoride), $SbCl_5$ (antimony pentachloride), $F_3CSO_3H$ (trifluoromethane sulfonic acid), as well as protic acids such as $HBF_4$ (tetrafluoroboric acid), $H_2SO_4$ (sulfuric acid), and combinations thereof, and the like.

The acid catalyst used in step (a) of the process of the present invention is typically employed in an amount of between about 0.01% and about two weight percent based upon the weight of the alkoxylated precursor-forming reaction mixture, preferably between about 50 and about 1,500 ppm in the reaction mixture. Exceeding the two percent upper limit of catalyst may result in undesirable side reactions.

The base catalyst(s) useful in the process of the present invention is preferably selected from the group consisting of alkali metal hydroxides and alkaline earth metal hydroxides, alkali metal alkoxides, and combinations thereof. Typical base catalysts include potassium hydroxide, sodium hydroxide, magnesium hydroxide, calcium hydroxide, sodium methoxide, potassium methoxide, sodium ethoxide, potassium ethoxide, and combinations thereof. The base catalyst is typically employed in an amount of between about 0.1% and about four percent by weight based upon the weight of the alkoxylated precursor-forming reaction mixture.

The alkylene oxide utilized in steps (a) and (b) of the process of the present invention is preferably propylene oxide, although other alkylene oxides such as ethylene oxide, butylene oxide, amylene oxide, hexylene oxide, and aralkylene oxides such as styrene oxide, and the like, are within the scope of the present invention. Random or block addition of the oxyalkylene groups is suitably made in accordance with the process of the present invention. In the preparation of lubricants, oxyalkylene groups of 3 or more carbons are preferred since shorter chain groups tend to attract water to an extent sufficient to cause corrosion in the heat transfer equipment.

In the preparation of lubricants, it is preferred that the halogenated polyoxylalkyene monoalcohol have a pour point of up to $-10°$ C., preferably $-20$ to $-50°$ C. In a case where the pour point exceeds $-10°$ C., a refrigerator oil composition containing such a high pour point lubricant is undesirably likely to solidify within the refrigeration system. In the preparation of lubricants, the number average molecular weight of the halogenated polyoxyalkylene monoalcohol preferably is between about 600 and about 3,000 to provide enhanced compressor sealability.

The lubricant of the present invention is typically utilized in conjunction with a heat transfer fluid which is a low boiling organic compound(s). Illustrative heat transfer fluids include acetone, methanol, hydrocarbons such as butane and isobutane, halocarbons such as chlorofluorocarbons ("CFCs"), hydrochlorofluorocarbons ("HCFCs"), dichloromethane, hydrofluorocarbons, combinations thereof, and the like.

In the formula for the halogenated polyoxyalkylene monoalcohol, $R_1$ is, for example, typically selected from the group of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl or octadeyl, or benzyl or substituted benzyl. The preferred moiety is selected from methyl ethyl, propyl, butyl, pentyl, hexyl, octyl, decyl, octadecyl, and benzyl. X is a halogen selected from the group consisting of fluorine, chlorine, bromine and iodine, and combinations thereof. Fluorine and chlorine are the most preferred halogens, and these are most advantageously utilized in the monoalcohol of the present invention as trifluoromethyl or trichloromethyl moieties. $R_2$ is preferably selected from the group consisting of ethylene, propylene, trimethylene, butylene, 1,2-dimethylethylene, 1-methyltriethylene, 2-methyltriethylene, tetramethylene and styrene, and combinations thereof. Of these, propylene, butylene and styrene are more preferred.

In the preparation of lubricants, it is also preferred that the kinematic viscosity of lubricant fall within the range of 15 to 500 cst at $100°$ F. In a case where the kinematic viscosity at $100°$ F. is less than 15 cst a refrigeration oil will not maintain a sufficient degree of sealability. In a case where the refrigeration oil composition is intended to be used in low temperature recompression devices, the halogenated polyoxyalkylene monoalcohol preferably has a kinematic viscosity of between 20 and 420 cst, more preferably 26 to 220 cst at $100°$ F. In addition, the halogenated polyoxyalkylene monoalcohol of this invention preferably has a weight average molecular weight of 600 to 3,000 to improve the compressor sealability.

The halogenated monoalcohol useful in the present invention is preferably trifluoroethanol, although other illustrative halogenated monoalcohols such as trichloroethanol, trifluoropropanol, dibromomonofluoroethanol, combinations thereof, and the like are within the scope of the present invention.

The double metal cyanide complex catalysts suitable for use in step (b) of the process of the present invention and their preparation are described in U.S. Pat. Nos. 4,472,560 and 4,477,589 to Shell Chemical Company and U.S. Pat. Nos. 3,941,849 and 4,335,188 to General Tire & Rubber Company. The teachings of the foregoing patents are incorporated herein by reference. The DMC catalyst used in step (b) of the process of the present invention is typically employed in an amount of between about 0.01% and about four weight percent based upon the weight of the step (b) reaction mixture.

One double metal cyanide complex catalyst found particularly suitable for use is a zinc hexacyanometallate of formula:

$Zn_3[M(CN)_6]_2 \cdot xZnCl_2 \cdot yGLYME \cdot zH_2O$ wherein M may be Co(III), or Cr(III) or Fe(II) or Fe(III); x, y, and z may be fractional numbers, integers, or zero and vary depending on the exact method of Preparation of the complex, preferably independently being between 0 and 15.

The process of the present invention is suitably conducted at a temperature of between about $20°$ C. and about $150°$ C., preferably between about $30°$ C. and about $120°$ C., although higher or lower temperatures may be used if desired. The reactions are suitably carried out at atmospheric pressure, although super- or sub-atmospheric pressures may be employed. The reaction times may vary from a few minutes to several hours or more depending upon the other reaction parameters.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited are incorporated herein by reference in their entirety.

The following examples are intended to illustrate, but in no way limit the scope of, the present invention.

EXAMPLE 1

Part A—Preparation of a Propoxylated Trifluoroethanol Precursor Using KOH Catalyst A precursor was prepared by reacting propylene oxide (PO) with trifluoroethanol using potassium hydroxide (KOH) as catalyst. When the reaction ceased, more KOH and PO were added until the reaction stopped. The reaction mixture was then treated using conventional treatment for removal of KOH. This treated product had a viscosity of 26.7 centistokes (cst) at 100° F. and a molecular weight of 600 as calculated from the hydroxyl number. Attempts to produce a higher molecular weight product using the KOH catalyst failed.

Part B—Preparation of a Propoxylated Trifluoroethanol Lubricant Using a Double Metal Cyanide Complex Catalyst Fifteen pounds (6.8 kg) of the precursor prepared in Part A was charged to a 10-gallon (36 liter) stainless steel reactor in ⅓ increments. The zinc hexacyanocobaltate glyme complex (DMC) catalyst, 0.015 pounds (6.8 grams) was dispersed into one of these additions of precursor. The reactor was sealed and purged with nitrogen.

The reactor was heated to 230±10° F. (110±6° C.) and 2.7 pounds (1.2 kg) of PO added. After an initiation period of about 1.5 to 2 hours, the reaction began as evidenced by a decrease in pressure and an increase in temperature. An additional 14.2 pounds (6.4 kg) of PO was added in a 2-hour period and post reacted to constant pressure in less than 1.5 hours. The viscosity at this point was 90 cst at 100° F., and the molecular weight was 1,160.

Even though the reaction mixture was cooled to about 100° F. (38° C.) and held overnight, the catalyst was still active the next day. An additional 5 pounds (2.3 kg) of PO was added at 230° F. (110° C.) in 70 minutes. Removal of catalyst residues was then effected. A typical catalyst removal procedure is as follows: the mixture is post-reacted for thirty minutes, and then KOH (0.055 pounds, 0.025 kg.) and a filter aid such as diatomaceous earth (0.185 pounds, 0.084 kg.) is added, and the resulting mixture is stirred at 110° C. for one hour, then vacuum stripped and filtered to provide a purified final product.

The final product had a viscosity of 109 cst at 100.0° F. (37.7° C.) and a hydroxyl number of 42.5. The calculated molecular weight for the product is 1,320.

Part C—Testing of the Product as a Lubricant

Miscibility Test

A miscibility determination was made by visually observing if the lubricant was clear to slightly hazy (and thus was designated "miscible") or was cloudy or phase separated (and thus was designated "immiscible") in R-134a (1,2,2,2-tetrafluoroethane) fluid. The product produced in Part B above was found to be miscible in R-134a at a concentration level of 10%, 20%, and 30% by weight. In contrast, a comparison formulation of polyoxylated n-butanol having a slighter lower molecular weight of 1,000 and containing no halogen was found to be immiscible in R-134a at a concentration level of 10% and a temperature of 120° F. Such immiscibility is unacceptable for a lubricant for R-134a.

As another comparison, another halogen-free monoalcohol, namely polyoxypropylene monobutylalcohol, having a higher molecular weight of 1850 was found to also be immiscible in R-134a at a concentration level of 20% and a temperature of 120° F. Such immiscibility is unacceptable for a lubricant for R-134a.

Although the propoxylated trifluoroethanol precursor produced in Part A above was found to be miscible in R-134a at a concentration level of 20%, this precursor had an undesirably low viscosity of 20 cst which is too low to function as an effective lubricant.

Four-Ball Test—ASTM-D-2783

This test was conducted in accordance with the ASTM procedure in order to measure the "Load Wear Index" or LWI as an indicator of the lubricating efficacy of the product produced in Part B above. Briefly, this ASTM procedure is conducted with one steel ball under load rotating against three steel balls held stationary in the form of a cradle. Test lubricant covers the lower three balls, and the rotating speed is 1760 rpm plus or minus 40 rpm. The testing apparatus and test lubricant are brought up to a temperature of 18–35° C. and then a series of duration tests are conducted until welding occurs.

Following this testing regimen, the product produced in Part B above was found to have an LWI of 25.5. In contrast, a comparison formulation was tested employing a halogen-free polyoxypropylene monobutylalcohol lubricant, having a lower molecular weight of 750 and viscosity of 35 cst at 100° F., and this comparison formulation provided an LWI of only 20.9.

EXAMPLE 2

Part A—Preparation of a Propoxylated Trifluoroethanol Precursor Using Antimony Pentafluoride as a Catalyst 2,2,2-trifluoroethanol (50 grams, 0.50 equivalent) was added to a flask under nitrogen, and antimony pentafluoride (0.05 grams, 0.23 miliequivalent) was added to the flask. Propylene oxide (200 grams, 3.44 equivalents) was added dropwise over a period of one hour. After stirring for an additional 15 minutes, the temperature was raised to 65° C. and the fact that no PO refluxed indicated that the reaction was complete. The product had a hydroxyl number of 112.

In a similar manner propoxylated trifluoroethanol precursors were prepared with $BF_3$ and $SbCl_5$ catalysts.

Part B—Preparation of a Propoxylated Trifluoroethanol Lubricant with Double Metal Cyanide Catalyst and a Precursor Prepared with SbF$_5$ A portion of the precursor prepared with SBF$_5$ catalyst described in Part A (100 g, 0.20 eq.) was added to a one liter autoclave without removal of the antimony pentafluoride and zinc hexacyanocobaltate glyme catalyst (0.64 g) was added and the mixture was heated to 100 C. Propylene oxide (30 g, 0.52 eq.) was added and after 20 minutes a pressure drop indicated that the catalyst was activated. An additional 428 grams of PO (7.4 eq.) was added over a 90 minute period and the pressure remained below 30 psi indicating that the PO was reacting rapidly. When the pressure fell below 10 psi, powdered KOH (2.5 g, 0.045 eq.) was added, and the mixture was heated at 110° C. for 1 hour. Magnesium silicate was added and the mixture was stirred at 110° C. for another hour then vacuum stripped for 2 hours and then filtered. The product had a hydroxyl number of 20.1 and a calculated molecular weight of 2,790 and was useful as a lubricant.

EXAMPLE 3

Preparation of a High Molecular Weight Propoxylated Trifluoroethanol Lubricant

A propoxylated trifluoroethanol precursor was prepared with SbCl$_5$ as described in Example 2 and 100 g (0.2 eq.) of this precursor was added to a one liter autoclave. Zinc hexacyanocobaltate glyme catalyst (0.64 g) was added and the mixture was flushed three times with nitrogen and heated to 100° C. Propylene oxide (30 g, 0.52 eq.) was added and after 20 minutes a pressure drop indicated that the catalyst was activated. An additional 570 g (9.81 eq.) of PO were added over a period of 90 minutes. When the pressure fell below 10 psi, 550 g of the mixture was removed from the reactor to allow for addition of more oxide. To the 150 g remaining in the reactor (150 g, 3,704 eq. wt., 0.0405 eq.) was added an additional 175 grams of PO over a period of 1 hour. After a post reaction of 30 minutes, KOMe (1.6 g) was added, and the mixture was heated at 110° C. for 1 hour. Magnesium silicate 4.9 g was added and the mixture was heated at 110 C for an additional hour and then vacuum stripped for 2 hours. The mixture was then filtered to yield a product with a hydroxyl number of 7.0 and a calculated molecular weight of 8,000.

What is claimed is:

1. A heat transfer composition comprising a heat transfer medium and a lubricant, wherein said heat transfer medium is a low boiling organic compound and wherein said lubricant is a halogenated polyoxyalkylene monoalcohol having the empirical structural formula:

$R_1X_m(OR_2)_n$—OH wherein R$_1$ is selected from the group consisting of a straight or branched-chain alkyl group having 1 to 18 carbon atoms, an aryl group having from 6 to 18 carbon atoms, and combinations thereof, wherein R$_2$ is selected from the group consisting of a straight or branched-chain alkylene group having 1 to 18 carbon atoms, an arylene group having from 6 to 18 carbon atoms, and combinations thereof, X is a halogen, m is an integer of between 1 and 37, and n is an integer from 5–350.

2. The heat transfer composition of claim 1 wherein said heat transfer medium comprises a chlorofluorocarbon, a hydrofluorocarbon, a fluorocarobon, or a combination thereof.

3. The composition of claim 1 wherein n has a value of between 10 and 50.

4. The composition of claim 1 wherein said lubricant has a molecular weight of at least about 500 and a viscosity of between about 20 cst and about 320 cst.

5. A process for producing a halogenated polyoxyalkylene monoalcohol having a molecular weight of between about 500 and about 20,000 by a reaction comprising:

(a) alkoxylating a halogenated monoalcohol in the presence of an acid or base catalyst to produce an alkoxylated halogenated monoalcohol having a molecular weight of between about 200 and about 500, and (b) reacting said alkoxylated halogenated monoalcohol with an alkylene oxide in the presence of a double metal cyanide catalyst to produce a halogenated polyoxyalkylene monoalcohol having a molecular weight of between about 500 and about 20,000.

6. The process of claim 5 wherein the catalyst of step (a) is a base catalyst selected from the group consisting of alkali metal hydroxides, alkaline earth metal hydroxides, alkali metal alkoxides, and combinations thereof, and wherein removal of base catalyst residues is effected prior to carrying out step (b).

7. The process of claim 5 wherein the catalyst of step (a) is an acid catalyst and wherein steps (a) and (b) are carried out simultaneously without removal of step (a) catalyst residues prior to carrying out step (b).

8. The process of claim 5 wherein the catalyst of step (a) is an acid catalyst and wherein steps (a) and (b) are carried out sequentially without removal of step (a) catalyst residues prior to carrying out step (b).

9. The process of claim 5 wherein the catalyst of step (a) is an acid catalyst selected from the group consisting of: BF$_3$Et$_2$O (boron trifluoride etherate), SbF$_5$ (antimony pentafluoride), SbCl$_5$ (antimony pentachloride), F$_3$CSO$_3$H (trifluoromethane sulfonic acid), HBF$_4$ (tetrafluoroboric acid), H$_2$SO$_4$ (sulfuric acid), and combinations thereof.

10. The process of claim 5 wherein the catalyst of step (a) is an acid catalyst employed in an amount of between about 0.01% and about two weight percent based upon the weight of the step (a) reaction mixture.

11. The process of claim 5 wherein the catalyst of step (a) is an acid catalyst employed in an amount of 50 and about 1,500 ppm in the step (a) reaction mixture.

12. The process of claim 5 wherein the catalyst of step (a) is a base catalyst employed in an amount of between about 0.1% and about four percent by weight based upon the weight of the step (a) reaction mixture.

13. The process of claim 5 wherein the double metal cyanide catalyst of step (b) is employed in an amount of between about 0.01% and about four weight percent based upon the weight of the step (b) reaction mixture.

* * * * *